(12) United States Patent
Kishioka et al.

(10) Patent No.: US 12,429,456 B2
(45) Date of Patent: Sep. 30, 2025

(54) DEVICE FOR MEASURING ELECTROLYTE CONCENTRATION

(71) Applicant: Hitachi High-Tech Corporation, Tokyo (JP)

(72) Inventors: Atsushi Kishioka, Tokyo (JP); Masafumi Miyake, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 514 days.

(21) Appl. No.: 17/799,893

(22) PCT Filed: Feb. 2, 2021

(86) PCT No.: PCT/JP2021/003752
§ 371 (c)(1),
(2) Date: Aug. 15, 2022

(87) PCT Pub. No.: WO2021/181947
PCT Pub. Date: Sep. 16, 2021

(65) Prior Publication Data
US 2023/0087708 A1     Mar. 23, 2023

(30) Foreign Application Priority Data

Mar. 9, 2020 (JP) ................................. 2020-040028

(51) Int. Cl.
*G01N 27/447* (2006.01)
(52) U.S. Cl.
CPC .............................. *G01N 27/44734* (2013.01)
(58) Field of Classification Search
CPC ....... G01N 27/44734; G01N 33/48707; G01N 27/4166
See application file for complete search history.

(56) References Cited

U.S. PATENT DOCUMENTS

2019/0265187 A1   8/2019 Kishioka et al.
2021/0165009 A1*  6/2021 Miyakawa ......... G01N 35/1002
(Continued)

FOREIGN PATENT DOCUMENTS

CN        1755355 A    4/2006
CN      109416338 A    3/2019
(Continued)

OTHER PUBLICATIONS

JP 3502466B2, English machine translation (Year: 1996).*

*Primary Examiner* — Luan V Van
*Assistant Examiner* — Randall Lee Gamble, Jr.
(74) *Attorney, Agent, or Firm* — PROCOPIO, CORY, HARGREAVES & SAVITCH LLP

(57) ABSTRACT

An object of the present invention is to provide a device for measuring electrolyte concentration capable of easily measuring a temperature difference between a sensitive membrane and liquid in the vicinity of the sensitive membrane that affects an electrolyte concentration analysis value. The device for measuring electrolyte concentration according to the present invention measures potential of an ion selective electrode at at least two or more different times while liquid is present in a flow path for introducing the liquid into the ion selective electrode, and calculates a temperature difference between the liquid and the ion selective electrode using the measured potential of the ion selective electrode at two or more different times (see FIG. 4).

17 Claims, 7 Drawing Sheets

(56) References Cited

U.S. PATENT DOCUMENTS

2021/0318266 A1* 10/2021 Kishioka .............. G01N 27/333
2021/0382000 A1* 12/2021 Fukaya .............. G01N 35/1009

FOREIGN PATENT DOCUMENTS

| JP | H08220062 A | 8/1996 |
| JP | 3502466 B2 * | 3/2004 |
| JP | 2007093252 A | 4/2007 |

* cited by examiner

DEVICE FOR MEASURING ELECTROLYTE CONCENTRATION

TECHNICAL FIELD

The present invention relates to a device for measuring electrolyte concentration that measures electrolyte concentration in liquid.

BACKGROUND ART

A flow-type device for measuring electrolyte concentration is mounted on a biochemical automatic analysis device or the like, and is characterized by analyzing electrolyte concentration in a specimen such as serum or urine with high accuracy and high throughput. The flow-type device for measuring electrolyte concentration is usually equipped with a plurality of ion selective electrodes corresponding to ions to be detected in order to simultaneously analyze the concentrations of a plurality of types of ions (sodium ion, potassium ion, chloride ion, and the like).

In order to perform accurate ion concentration analysis using an ion selective electrode, it is important under the measurement principle to set temperatures of liquid to be measured and the electrode to the same temperature (to be uniform). For this reason, conventionally, there is a device having a temperature sensor and a temperature control mechanism.

PTL 1 below discloses a technique in which "a sample temperature control block is provided in a flow path from a sample suction nozzle to an electrode block, a sensor that measures a temperature of the electrode block, of the sample temperature control block, and of outside air is mounted in various places, and output control is performed on a heater installed in each block according to an outside air temperature so that temperatures of an ion selective electrode, of a reference electrode, of reference electrode internal liquid, of a sample when reaching each electrode flow path, and of calibration liquid become the same temperature, thereby eliminating influence of the outside air temperature" (see Abstract).

PTL 2 below discloses a technique of "an electrolyte measurement device that brings test liquid flowing in a flow path into contact with a membrane electrode and measures electrolyte concentration based on voltage (potential difference) between the test liquid and the membrane electrode, including a plurality of types of membrane electrodes that measure voltage of the test liquid, a first temperature sensor that is installed on an upstream side of a plurality of types of the membrane electrodes in a flow path of the test liquid and measures a temperature of the test liquid, a second temperature sensor that is installed on a downstream side of a plurality of types of the membrane electrodes in the flow path of the test liquid and measures a temperature in the flow path of the test liquid, and a temperature compensating means that corrects measurement voltage by a plurality of types of the membrane electrodes based on a temperature value measured by the first temperature sensor and the second temperature sensor" (see Abstract).

CITATION LIST

Patent Literature

PTL 1: JP 2007-093252 A
PTL 2: JP H8-220062 A

SUMMARY OF INVENTION

Technical Problem

A value of potential (electromotive force) outputted from an ion selective electrode is affected not only by ion concentration in liquid (specimen) to be measured but also by temperature, which greatly affects an analysis result. Among them, it is particularly difficult to manage a temperature difference between an electrode and liquid to be analyzed in an electrolyte measurement device. More specifically, the temperature difference is a temperature difference between an ion sensitive membrane in an ion selective electrode and liquid in the vicinity of the ion sensitive membrane, and it is important to reduce this temperature difference. The reduction is particularly important under an environment where room temperature or the like is not stable, and for a small device or the like on which a sufficient temperature control mechanism cannot be mounted. However, it has been difficult to measure a temperature difference of this local portion.

In view of the above, as in PTLs 1 and 2, a temperature difference has been indirectly measured by attaching a temperature sensor in the vicinity of an electrode or a liquid flow path. For example, a temperature sensor has been attached to a housing wall surface or the like of an electrode instead of an ion sensitive membrane, or a temperature sensor has been attached upstream or downstream of an electrode flow path instead of liquid in the vicinity of an ion sensitive membrane. Therefore, there is a problem from the viewpoint of measurement accuracy of a temperature difference. Further, as described in PTL 2, when a temperature sensor is attached in a flow path, electrical noise due to the temperature sensor affects potential measurement, and thus there has also been a problem that an installation position of the temperature sensor is limited. Further, in an electrolyte analysis device of high throughput, since liquid in a flow path is replaced in a cycle of several seconds, it has been difficult to follow a change in liquid temperature because a temperature sensor itself has heat capacity, and it has been difficult to accurately measure temperature of liquid.

The present invention has been made in view of the above problem, and an object of the present invention is to provide a device for measuring electrolyte concentration capable of easily measuring a temperature difference between a sensitive membrane and liquid in the vicinity of the sensitive membrane that affects an electrolyte concentration analysis value.

Solution to Problem

A device for measuring electrolyte concentration according to the present invention measures potential of an ion selective electrode at at least two or more different times while liquid is present in a flow path for introducing the liquid into the ion selective electrode, and calculates a temperature difference between the liquid and the ion selective electrode using the measured potential of the ion selective electrode at two or more different times.

Advantageous Effects of Invention

According to the device for measuring electrolyte concentration of the present invention, it is possible to easily measure a temperature difference between a sensitive membrane and liquid in the vicinity of the sensitive membrane without adding a temperature sensor. Furthermore, output of a temperature control mechanism can be controlled or a potential value can be corrected using information of the measured temperature difference. This leads to improvement in reliability of an analysis value. Objectives, configurations, and advantageous effects other than those described above will be clarified in description of embodiments described below.

DESCRIPTION OF EMBODIMENTS

In order to realize more stable analysis in a device for measuring electrolyte concentration, the inventors have conducted research and development on a method of suppressing fluctuation with respect to temperature. As a result, it has been found that a temperature difference measurement between an ion sensitive membrane and liquid in the vicinity of the ion sensitive membrane, which has been conventionally difficult, can be calculated from potential measured by an ion selective electrode. Further, by utilizing information of the temperature difference, a device for performing more stable analysis has been realized.

First Embodiment

Figure 1:
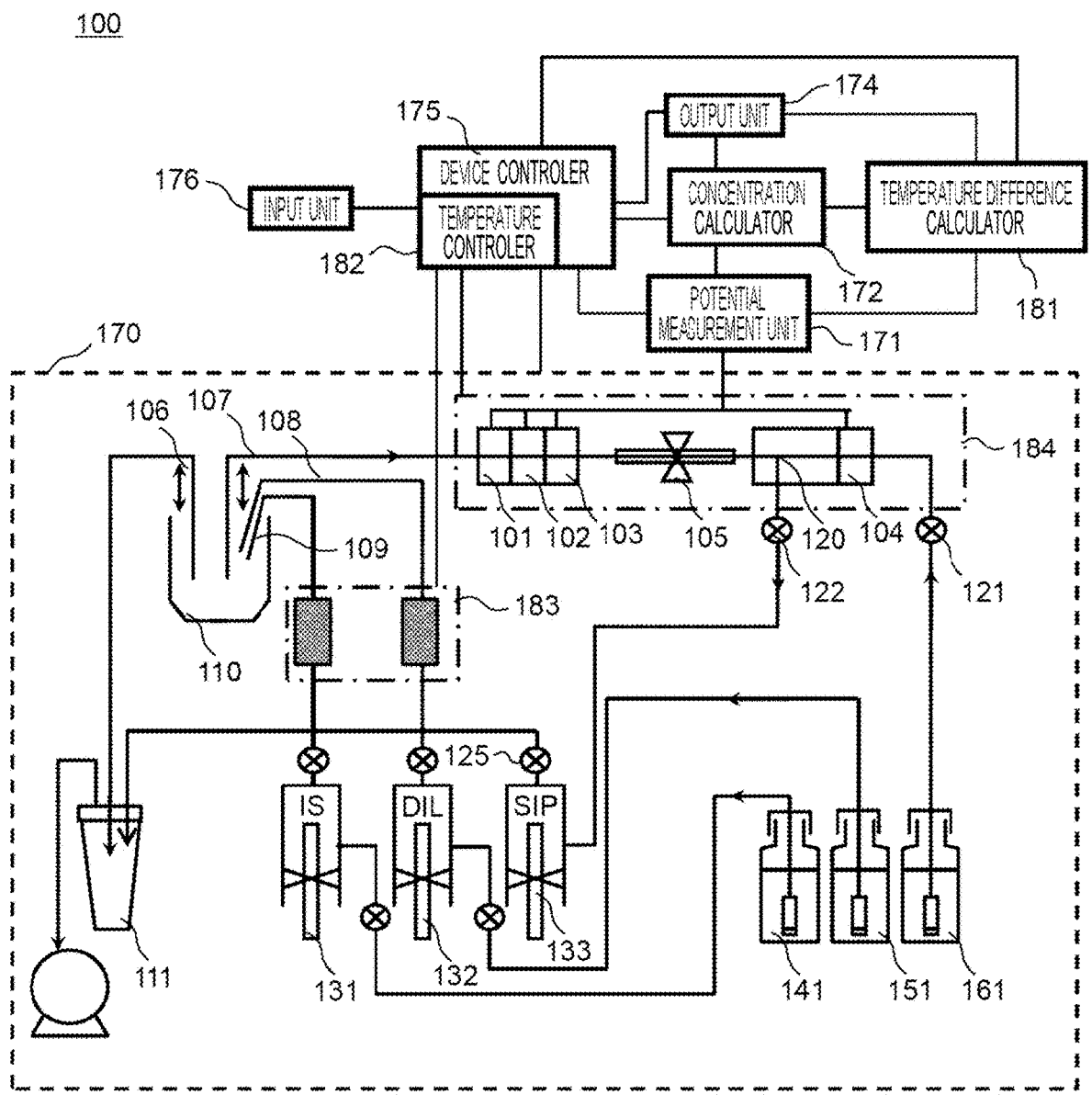
FIG. 1 is a schematic view illustrating a configuration example of a flow-type device 100 for measuring electrolyte concentration according to a first embodiment.

FIG. 1 is a schematic view illustrating a configuration example of a flow-type device 100 for measuring electrolyte concentration according to a first embodiment of the present invention. The device 100 for measuring electrolyte concentration includes a measurement unit 170, a potential measurement unit 171, a concentration calculator 172, an output unit 174, a device controller 175, a temperature controller 182, an input unit 176, and a temperature difference calculator 181.

The measurement unit 170 includes three types of electrodes of a chlorine ion electrode 101, a potassium ion electrode 102, and a sodium ion electrode 103, which are ion selective electrodes, and a comparative electrode 104. An electrode having a flow path diameter of 1 mm is used. A dilution tank 110 is filled with a diluted specimen in which a specimen dispensed from a specimen nozzle (not illustrated) and a diluent dispensed from a diluent supply nozzle 108 are mixed, or is filled with internal standard solution dispensed from an internal standard solution supply nozzle 109. A sipper nozzle 107 descends into the dilution tank 110, and the diluted specimen or internal standard solution with which the dilution tank 110 is filled is introduced into a flow path of the ion selective electrode by a sipper syringe pump 133. Further, comparative electrode liquid is introduced from a comparative electrode liquid bottle 161 into a flow path of the comparative electrode 104 using the sipper syringe pump 133. During this time, the diluted specimen or the internal standard solution remaining in the dilution tank is sucked by a vacuum suction nozzle 106 descending into the dilution tank and is discharged to a waste liquid tank 111.

A temperature controller 182 is arranged in a device controller 175, and performs temperature control of a reagent temperature control mechanism 183 and an electrode temperature control mechanism 184. The reagent temperature control mechanism 183 and the electrode temperature control mechanism 184 include, for example, a heater and a temperature sensor. The reagent temperature control mechanism 183 has a function of controlling temperature of a reagent, and the electrode temperature control mechanism 184 has a function of controlling temperature of a measurement flow path including an electrode. A temperature sensor of the electrode temperature control mechanism 184 is embedded in a block in the vicinity of an electrode, and monitors temperature of an electrode housing.

Detailed operation of a mechanism portion when a measurement flow path is filled with liquid will be described. First, when the liquid with which the dilution tank is filled is introduced into the flow path of the ion selective electrode, an electromagnetic valve 121 and an electromagnetic valve 125 are closed, a pinch valve 105 and an electromagnetic valve 122 are opened, the sipper nozzle 107 is lowered into the dilution tank, and the sipper syringe pump 133 is pulled. Subsequently, when the comparative electrode liquid is introduced into a flow path of the comparative electrode, the sipper nozzle is raised, the electromagnetic valve 121 is opened, the pinch valve 105 is closed, and the sipper syringe pump 133 is pulled, so that the comparative electrode liquid is introduced from a comparative electrode liquid bottle 161 into a flow path of the comparative electrode 104. After the above, in a state where the electromagnetic valve 121 is closed and the pinch valve 105 is opened, potential between the ion selective electrode and the comparative electrode is measured by the potential measurement unit 171. In order to discharge liquid accumulated in a sipper syringe, the electromagnetic valve 122 is closed, the electromagnetic valve 125 is opened, and the sipper syringe pump 133 is pushed.

Figure 3:
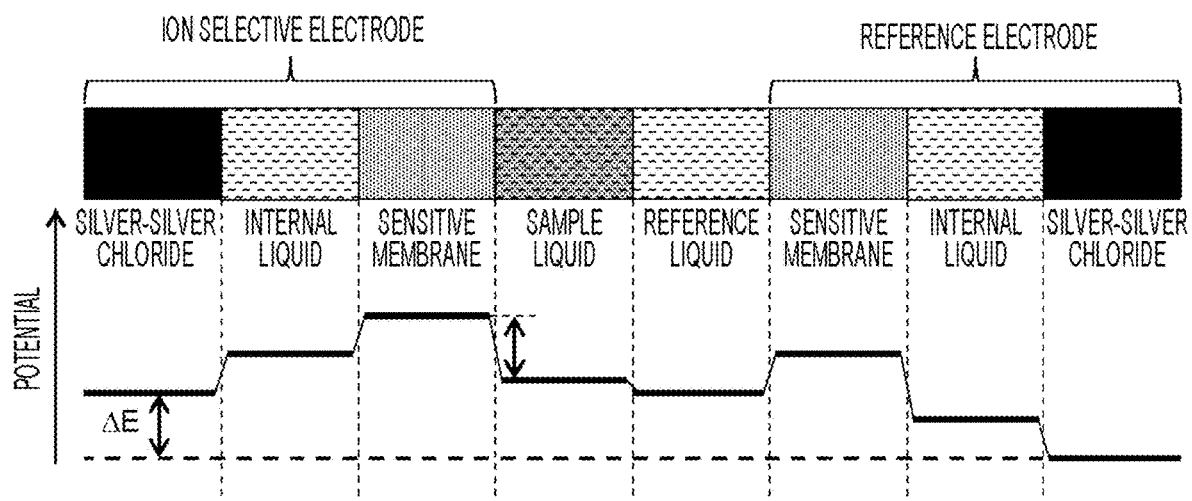
FIG. 3 is a schematic diagram illustrating a concept of potential distribution at each constituent interface between a terminal of an ion selective electrode and a terminal of a reference electrode.

The comparative electrode liquid introduced into the flow path of the comparative electrode and the liquid introduced into the ion selective electrode are brought into contact with each other in a liquid junction portion 120, and the ion selective electrode and the comparative electrode are in a state of being electrically connected to each other through the liquid. Although details will be described later, a schematic diagram of potential distribution between terminals at this time is illustrated in FIG. 3. Since a potential difference (electromotive force) between the comparative electrode and each ion selective electrode changes depending on concentration of ions to be analyzed in the liquid introduced into the flow path of the ion selective electrode, the potential measurement unit 171 measures the electromotive force, and the concentration calculator 172 calculates ion concentration using a measurement result of the electromotive force. The temperature difference calculator 181 calculates a temperature difference between an ion sensitive membrane and a specimen in the vicinity of the ion sensitive membrane from the potential change measured by the potential measurement unit 171. Details of these calculation methods will be described later. Since the potential of the comparative electrode is used as a reference, the electromotive force measured by the potential measurement unit 171 can be handled as potential of the ion selective electrode.

Figure 2:
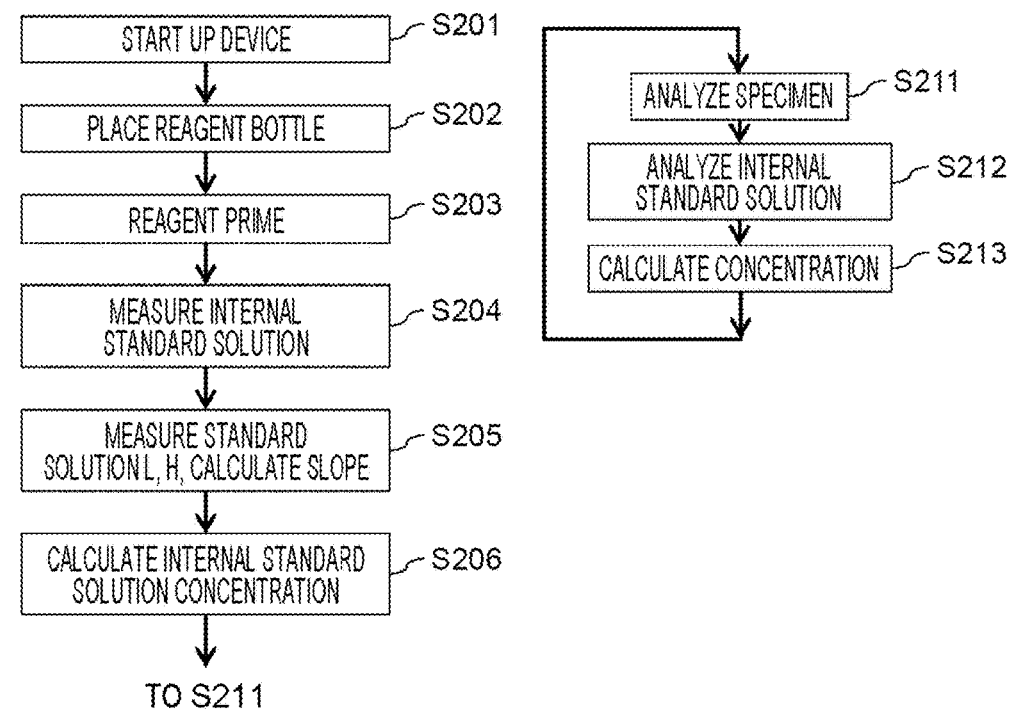
FIG. 2 is a flowchart for explaining a procedure in which the device 100 for measuring electrolyte concentration measures electrolyte concentration.

FIG. 2 is a flowchart for explaining a procedure in which the device 100 for measuring electrolyte concentration measures electrolyte concentration. First, a procedure at the time of device start-up will be described. The device is started up (S201), and a reagent bottle is placed (S202). Reagent prime is performed to replace and fill the inside of the syringe pump and the flow path with a new reagent (S203). After temperature control, the internal standard solution is measured to confirm that potential of the electrode is stable (S204). In order to obtain a calibration curve of the ion selective electrodes 101, 102, and 103, two types of standard solution having known concentration are measured, and a slope is calculated (S205). Subsequently, internal standard solution concentration is calculated (S206).

Specific operation in S205 and S206 will be described. After known low-concentration standard solution is dispensed into the dilution tank 110 with a dispensing nozzle (not illustrated), a diluent in a diluent bottle 151 is dispensed into the dilution tank using a diluent syringe pump 132, and the known low-concentration standard solution is diluted at a preset ratio D. The diluted known low-concentration standard solution in the dilution tank is sucked from the sipper nozzle 107 and introduced into a flow path of the ion selective electrodes 101, 102, and 103. After the above, comparative electrode liquid is introduced into a flow path of the comparative electrode 104 from the inside of the comparative electrode liquid bottle 161. In the liquid junction portion, the comparative electrode liquid and the diluted known low-concentration standard solution come into contact with each other. Each potential difference (electromotive force) between the ion selective electrodes 101, 102, and 103 and the comparative electrode 104 is respectively measured by the potential measurement unit 171.

During the measurement, remaining liquid in the dilution tank is sucked up by the vacuum suction nozzle, and then internal standard solution in an internal standard solution bottle 141 is dispensed into the dilution tank by an internal standard solution syringe pump 131. The internal standard solution in the dilution tank is sucked from the sipper nozzle 107, a flow path of the ion selective electrodes 101, 102, and 103 is filled with the internal standard solution, comparative electrode liquid is introduced from the inside of the comparative electrode liquid bottle 161 into a flow path of the comparative electrode 104, and an electromotive force of each electrode is measured by the potential measurement unit 171.

During the measurement, remaining liquid in the dilution tank is sucked up by the vacuum suction nozzle, and then after known high-concentration standard solution is dispensed into the dilution tank 110 with a dispensing nozzle (not illustrated), a diluent in the diluent bottle 151 is dispensed into the dilution tank using the diluent syringe pump 132, and the known high-concentration standard solution is diluted at the preset ratio D. The diluted known high-concentration standard solution in the dilution tank is sucked from the sipper nozzle and introduced into a flow path of the ion selective electrodes 101, 102, and 103. After the above, comparative electrode liquid is introduced into a flow path of the comparative electrode 104 from the inside of the comparative electrode liquid bottle 161. In the liquid junction portion, the comparative electrode liquid and the diluted known high-concentration standard solution come into contact with each other. Each potential difference (electromotive force) between the ion selective electrodes 101, 102, and 103 and the comparative electrode 104 is respectively measured by the potential measurement unit 171.

During the measurement, remaining liquid in the dilution tank is sucked up by the vacuum suction nozzle, and then internal standard solution in the internal standard solution bottle 141 is dispensed into the dilution tank. The internal standard solution in the dilution tank is sucked from the sipper nozzle, a flow path of the ion selective electrodes 101, 102, and 103 is filled with the internal standard solution, comparative electrode liquid is introduced from the inside of the comparative electrode liquid bottle 161 into a flow path of the comparative electrode 104, and an electromotive force of each electrode is measured by the potential measurement unit 171. Further, remaining liquid in the dilution tank is sucked up by the vacuum suction nozzle.

The potential measurement unit 171 acquires potential of each ion selective electrode every 10 ms in a state where liquid is stationary during a period from introduction of liquid to be measured into the flow path until introduction of next liquid. The concentration calculator 172 calculates ion concentration in liquid from an average value of potentials at last ten points (ten points immediately before the next liquid is introduced) acquired by the potential measurement unit 171. Since the number of potentials used for concentration calculation is one, the number of measurement points does not need to be ten, but may be one or more. Since the potential measurement is affected when a mechanism component connected to a measured flow path is driven, stable potential at a timing the mechanism is not moving is suitable. As a potential acquisition interval, a method of selecting a potential value used for calculation, and the like, those other than the above may be used.

The concentration calculator 172 calculates slope sensitivity SL corresponding to a calibration curve from an electromotive force measured by the potential measurement unit 171 using a calculation formula below.

(A) Slope Sensitivity $$SL = (EMFH - EMFL)/(\text{Log } CH - \text{Log } CL) \quad \text{Equation (1)}$$

SL: slope sensitivity

EMFH: measured electromotive force (potential) of known high-concentration standard solution EMFL: measured electromotive force (potential) of known low-concentration standard solution CH: known concentration value of high-concentration standard solution CL: known concentration value of low-concentration standard solution The above operation is referred to as calibration. The slope sensitivity SL corresponds to $2.303 \times (RT/zF)$ in the Nernst equation:

$$E = E0 + 2.303 \times (RT/zF) \times \log(f \times C)$$

E0: constant potential determined by measurement system
z: valence of ion to be measured
F: Faraday constant
R: gas constant
T: absolute temperature
f: activity coefficient
C: ion concentration. In theory, SL can be obtained by calculation from a temperature and a valence of an ion to be measured. However, in the present embodiment, the slope sensitivity SL unique to an electrode is obtained by the calibration in order to further improve analysis accuracy.

Subsequently, internal standard solution concentration is calculated from the slope sensitivity and an electromotive force of the internal standard solution.

(B) Internal Standard Solution Concentration $$CIS = CL \times 10^a \quad \text{Equation (2)}$$

$$a = (EMFIS - EMFL)/SL \quad \text{Equation (3)}$$

CIS: internal standard solution concentration
EMFIS: electromotive force (potential) of internal standard solution Although the specific calibration method is described above, a different procedure may be used as long as two or more types of liquid having different ion concentrations can be introduced into a flow path and an electromotive force can be measured regardless of this procedure.

Next, an operation at the time of continuous analysis will be described. After the above calibration, a specimen such as serum or urine is analyzed. Specifically, after a specimen is dispensed into the dilution tank 110 with a dispensing nozzle (not illustrated), a diluent in the diluent bottle 151 is dispensed into the dilution tank using the diluent syringe pump 132, and the specimen is diluted at the preset ratio D. The diluted specimen in the dilution tank is sucked from the sipper nozzle and introduced into a flow path of the ion selective electrodes 101, 102, and 103. After the above, comparative electrode liquid is introduced into a flow path of the comparative electrode 104 from the inside of the comparative electrode liquid bottle 161. In the liquid junction portion, the comparative electrode liquid and the diluted specimen come into contact with each other. A potential difference (electromotive force) between the ion selective electrodes 101, 102, and 103 and the comparative electrode 104 is measured by the potential measurement unit 171 (S211).

During the measurement, remaining liquid in the dilution tank is sucked up by the vacuum suction nozzle, and then internal standard solution in the internal standard solution bottle 141 is dispensed into the dilution tank. The internal standard solution in the dilution tank is sucked from the sipper nozzle, and a flow path of the ion selective electrodes 101, 102, and 103 is filled with the internal standard solution. The comparative electrode liquid is introduced from the inside of the comparative electrode liquid bottle 161 into a flow path of the comparative electrode 104, and an electromotive force of each electrode is measured by the potential measurement unit 171 (S212).

The remaining liquid in the dilution tank is sucked up by the vacuum suction nozzle. Note that liquid for refreshing may be introduced into the dilution tank or the flow path during the analysis.

From the slope sensitivity and the internal standard solution concentration, concentration of the specimen is calculated using a calculation formula below (S213).

(C) Concentration of Specimen $$CS = CIS \times 10^b \quad \text{Equation (4)}$$

$$b = (EMFIS - EMFS)/SL \quad \text{Equation (5)}$$

CS: specimen concentration
EMFS: measured electromotive force (potential) of specimen Although the specific calculation method is described above, other calculation formulas and correction formulas may be used.

In all the above calculation processes, calculation is performed using a potential value. Accordingly, in a case where potential changes due to a factor other than ion concentration, an analysis result is affected. In particular, temperature is one of major influence factors. From a value of measured potential of the internal standard solution having constant concentration measured before and after specimen measurement, it is possible to correct the analysis result with respect to relatively gentle temperature change. However, it is difficult to cope with a large temperature change.

Next, the temperature difference calculator 181 will be described. The temperature difference calculator 181 calculates a temperature difference between a sensitive membrane in an electrode and introduced liquid from potential data at every 10 ms when liquid is stationary acquired by the potential measurement unit 171. Specifically, a temperature difference model is analyzed by fitting a curve to time-series data of potential in each electrode. In a simple manner, the temperature difference model can be calculated from a slope of potential in each electrode. In this case, if there is a value of potential at two or more points acquired at different times, the temperature difference model can be calculated. A principle and a specific calculation method of calculating the temperature difference will be described below.

FIG. 3 is a schematic diagram illustrating a concept of potential distribution at each constituent interface between a terminal of an ion selective electrode and a terminal of a reference electrode. FIG. 3 is for illustration and does not represent an accurate actual state, and a direction and intensity of each potential difference vary depending on a case. At each interface of each constituent, a potential difference corresponding to the constituent is generated. A potential difference between terminals can be represented by the sum of interface potentials generated between each constituent. Since a constituent that changes for each measurement is only sample liquid (specimen) and a sensitive membrane of each ion selective electrode selectively responds to each ion to be measured, a change in a potential difference corresponds to a change in ion concentration of an ion to be measured in the sample liquid. The interface potential is expressed by the above-described Nernst equation. In a portion where sample liquid and reference liquid are in contact with each other (liquid junction portion), a potential difference represented by the Henderson's equation is generally generated. However, since a high-concentration KCl aqueous solution is used as the reference liquid, a change in liquid potential in the liquid junction portion due to a change in concentration of the sample liquid is negligibly small.

That is, the device 100 for measuring electrolyte concentration can indirectly measure a change in interface potential between a sensitive membrane of an ion selective electrode and sample liquid by measuring a potential difference (4E) between each ion selective electrode and a reference electrode based on potential of the reference electrode. However, the Nernst equation includes a temperature term, and an activity coefficient also shows temperature dependence. For this reason, it can be seen from the equation that even when the composition of liquid is the same, different interface potentials are exhibited when the temperature is different.

Next, an example in which a potential change due to a temperature difference between a sensitive membrane and sample liquid is experimentally confirmed will be described. Basically, a device having a configuration similar to that of the device 100 for measuring electrolyte concentration according to the present embodiment was used. However, the example is different from the present embodiment in that (a) liquids having different temperatures are intentionally introduced, (b) potential acquisition is always performed not only when liquid is stationary but also during liquid feeding, and (c) a thermocouple is attached to a flow path of an electrode. A thermocouple for temperature monitoring in a flow path was installed for this verification and is not necessary when implementing the present invention. As the thermocouple attached to a flow path, an ultrafine thermocouple having a small heat capacity was used so as to follow a temperature of liquid as much as possible. Since the thermocouple is in direct contact with liquid, electrical noise from the thermocouple affects a potential measurement result of an ion selective electrode. Since this is a principle verification experiment, the measurement was performed while the accuracy of potential measurement was sacrificed to some extent.

Figure 4:
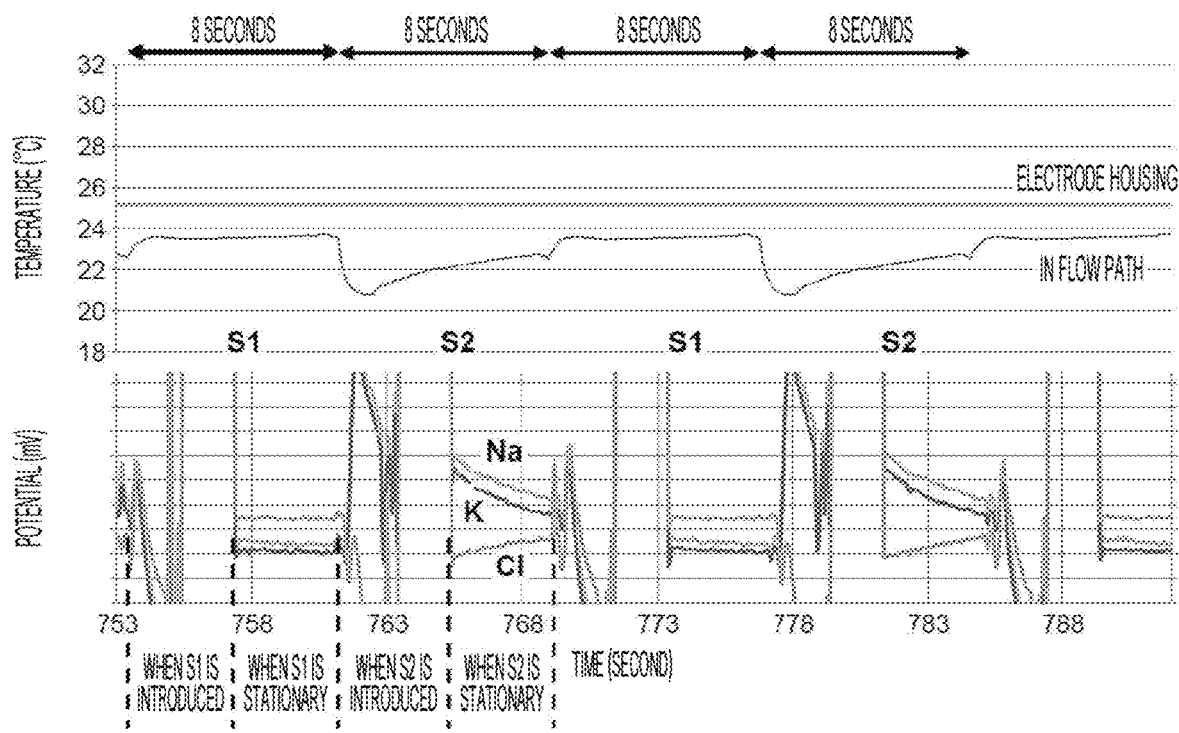
FIG. 4 shows a result of alternately and continuously measuring sample liquid S1 and S2 having the same ion concentration and different temperatures.

FIG. 4 shows a result of alternately and continuously measuring the sample liquid S1 and S2 having the same ion concentration and different temperatures. FIG. 4 shows a measurement result in a case where a temperature of an electrode and S1 are at about 25° C. and a temperature of only S2 is low. An upper graph of FIG. 4 shows a result of measuring a temperature of a wall surface of the electrode and a flow path of the electrode. A lower graph of FIG. 4 shows potential values obtained from three types of ion selective electrodes for Na, K, and Cl. Potential in the vertical axis indicates a value which is offset so as to fit in one graph, and the horizontal axis indicates time (second).

At the time of liquid introduction, an electromagnetic valve is opened and closed to feed sample liquid and comparative electrode liquid, and thus potential is disturbed. When liquid is stationary, potential of S1 is stable in all three types of electrodes. On the other hand, for S2 having a low temperature, potential fluctuates as described below. Potential of the Cl electrode starts from a value lower than that of S1, gradually increases, and approaches potential of S1. Potential of the Na and K electrodes starts from a value higher than that of S1, gradually decreases, and approaches potential of S1.

Figure 5:
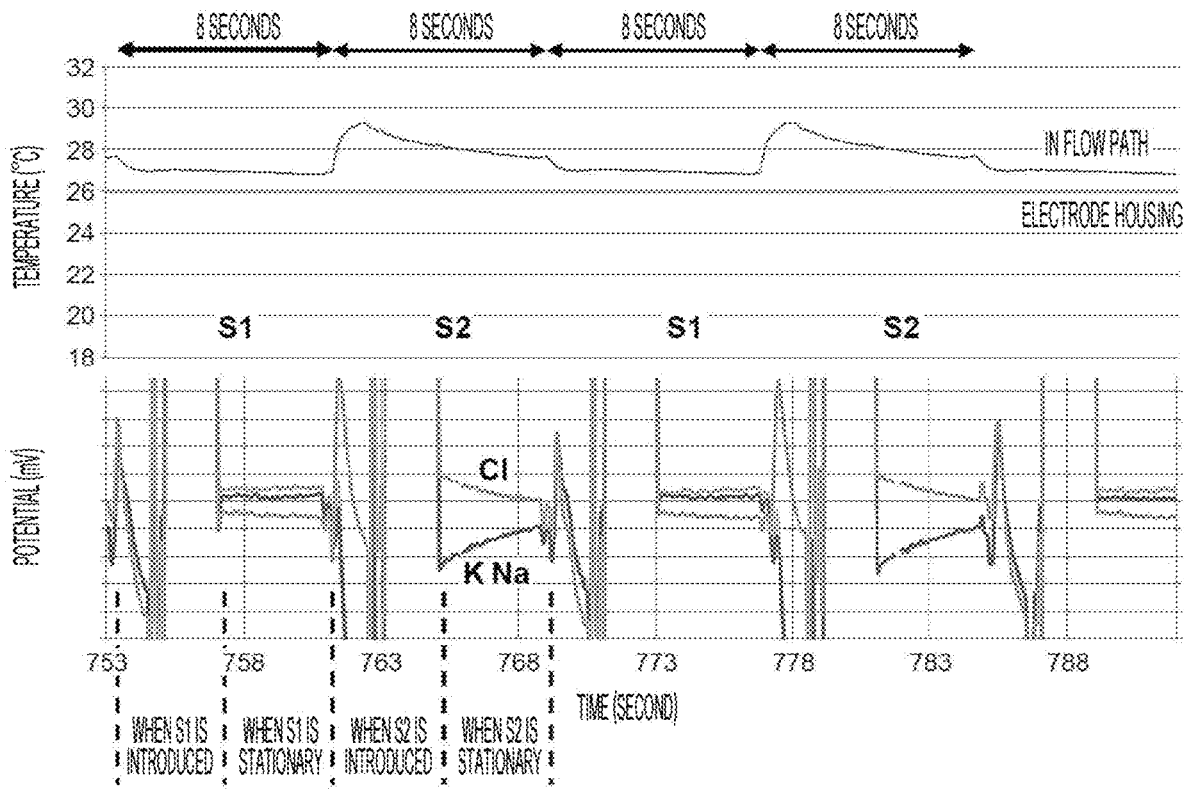
FIG. 5 shows a result of alternately and continuously measuring the sample liquid S1 and S2 having the same ion concentration and different temperatures.

FIG. 5 shows a measurement result in a case where a temperature of the electrode and S1 is about 26° C. and only S2 is at a high temperature. As in FIG. 4, potential of S1 when liquid is stationary was stable in all the three types of electrodes. On the other hand, potential of S2 when liquid is stationary fluctuates as described below. Potential of the Cl electrode starts at a value higher than that of S1, gradually decreases, and approaches potential of S1. Potential of the Na and K electrodes starts from a value lower than that of S1, gradually increases, and approaches potential of S1. That is, the tendency opposite to that in FIG. 4 is shown. Although S1 and S2 are liquid of the same concentration, such different potential fluctuations are caused by a change in temperature.

The reason why the Cl electrode and the Na and K electrodes showed opposite tendencies is considered to be that signs of the ions to be measured are different from each other such as an anion and a cation. The reason why potential of S2 when liquid is stationary starts from potential away from potential of S1 and gradually approaches the potential of S1 is considered as described below. Immediately after the introduction of the sample liquid S2 into a flow path, a temperature difference between the sample liquid and the ion sensitive membrane of the electrode is large, but it is considered that the temperature difference is gradually eliminated when liquid is stationary. In fact, temperature indicated by the thermocouple installed to measure liquid temperature in a flow path in FIG. 4 is around 24° C. when S1 is stationary, whereas the temperature steeply decreases to around 21° C. at the time of S2 introduction, and then the liquid temperature in the flow path gradually approaches temperature of the electrode when S2 is stationary. Since heat is exchanged between the liquid in the flow path and the electrode, and the temperature of the electrode is controlled, the temperature of the electrode is adjusted to the controlled temperature of the electrode if the liquid is stationary for a long time.

In FIG. 4, a slope (change amount) of potential of the Cl electrode when liquid of S2 is stationary is about a half of a slope of potential of the Na and K electrodes. The reason for this is considered to be that a sensitive membrane of the Cl electrode used in the measurement is thinner than a sensitive membrane of the Na and K electrodes. When liquid different from temperature of an electrode is introduced into a flow path, a temperature difference occurs between the front and back of a sensitive membrane. When the sensitive membrane is thin, this temperature difference is quickly eliminated, but when the membrane is thick, the temperature difference is slowly eliminated. When temperature of an interface on the flow path side (front side) and temperature of an interface on the internal liquid side (back side) of the sensitive membrane change in the same manner, a potential change occurs in a direction in which the front and back cancel each other. However, when only temperature of one interface changes, an effect of canceling each other does not occur, and it is considered that a large potential fluctuation occurs. From this, it is considered that as membrane thickness is thinner, a temperature difference between the front and back of the membrane is rapidly reduced, and a potential fluctuation is alleviated early. Note that, when a Na electrode with changed membrane thickness was prepared and the same measurement was performed, it was confirmed that a potential fluctuation due to a temperature change of liquid in a flow path decreases as the membrane thickness decreases.

Further, experiments were performed at various temperatures other than the temperatures of S1 and S2 shown in FIGS. 4 and 5. Then it was confirmed that the larger the temperature difference between the electrode and the sample liquid, the larger the potential fluctuation.

Figure 6:
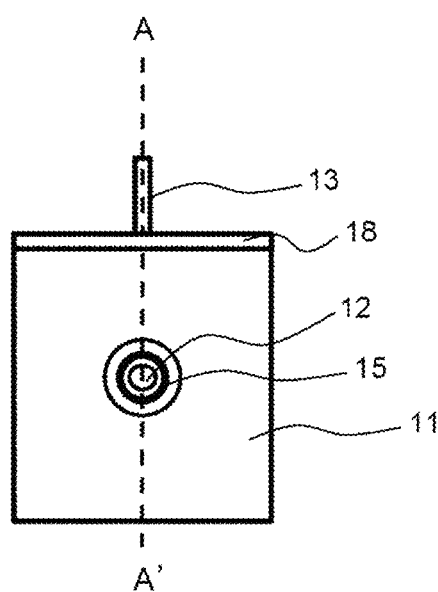
FIG. 6 is a front view of the ion selective electrode included in the device 100 for measuring electrolyte concentration.
Figure 7:
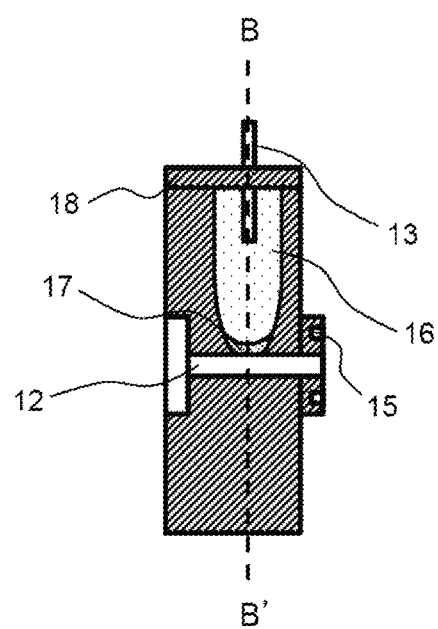
FIG. 7 is a cross-sectional view taken along line A-A' of FIG. 6.
Figure 8:
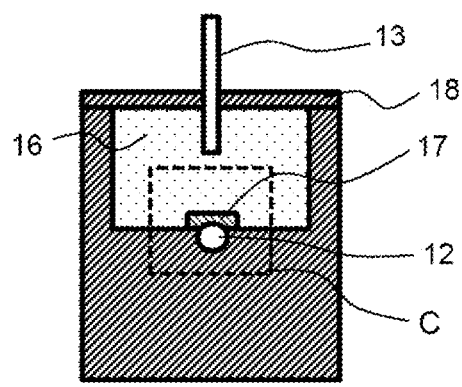
FIG. 8 is a cross-sectional view taken along line B-B' of FIG. 7.

FIG. 6 is a front view of the ion selective electrode included in the device 100 for measuring electrolyte concentration. FIG. 7 is a cross-sectional view taken along line A-A' of FIG. 6. FIG. 8 is a cross-sectional view taken along line B-B' of FIG. 7. The ion selective electrode has a flow path 12 penetrating an electrode housing 11, and sample liquid to be measured passes through the flow path 12. An ion sensitive membrane 17 is provided so as to be in contact with the sample liquid, and internal liquid 16 containing an electrolyte so as to fill the electrode housing is further provided. An internal electrode 13 is provided so as to be in contact with the internal liquid 16, and a lid 18 is bonded in order to confine the internal liquid in the electrode housing. Packing 15 is provided in the vicinity of an inlet and an outlet of the flow path 12 of the electrode housing so as to be connectable to the device or a flow path of another electrode. The ion selective electrode is mounted on the device 100 for measuring electrolyte concentration shown in FIG. 1, and the internal electrode 13 is connected to a wiring on the device side, so that potential generated according to concentration of an ion to be measured contained in the sample liquid can be measured.

Figure 9:
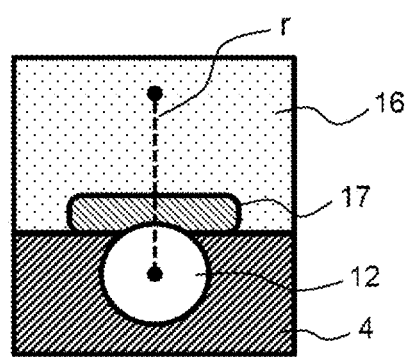
FIG. 9 is an enlarged schematic view of a portion C in FIG. 8.

FIG. 9 is an enlarged schematic view of a portion C in FIG. 8. The flow path center in an end portion of a dotted line r in FIG. 9 is set to r=0 mm, and temperature distribution at each position will be described below.

Figure 10:
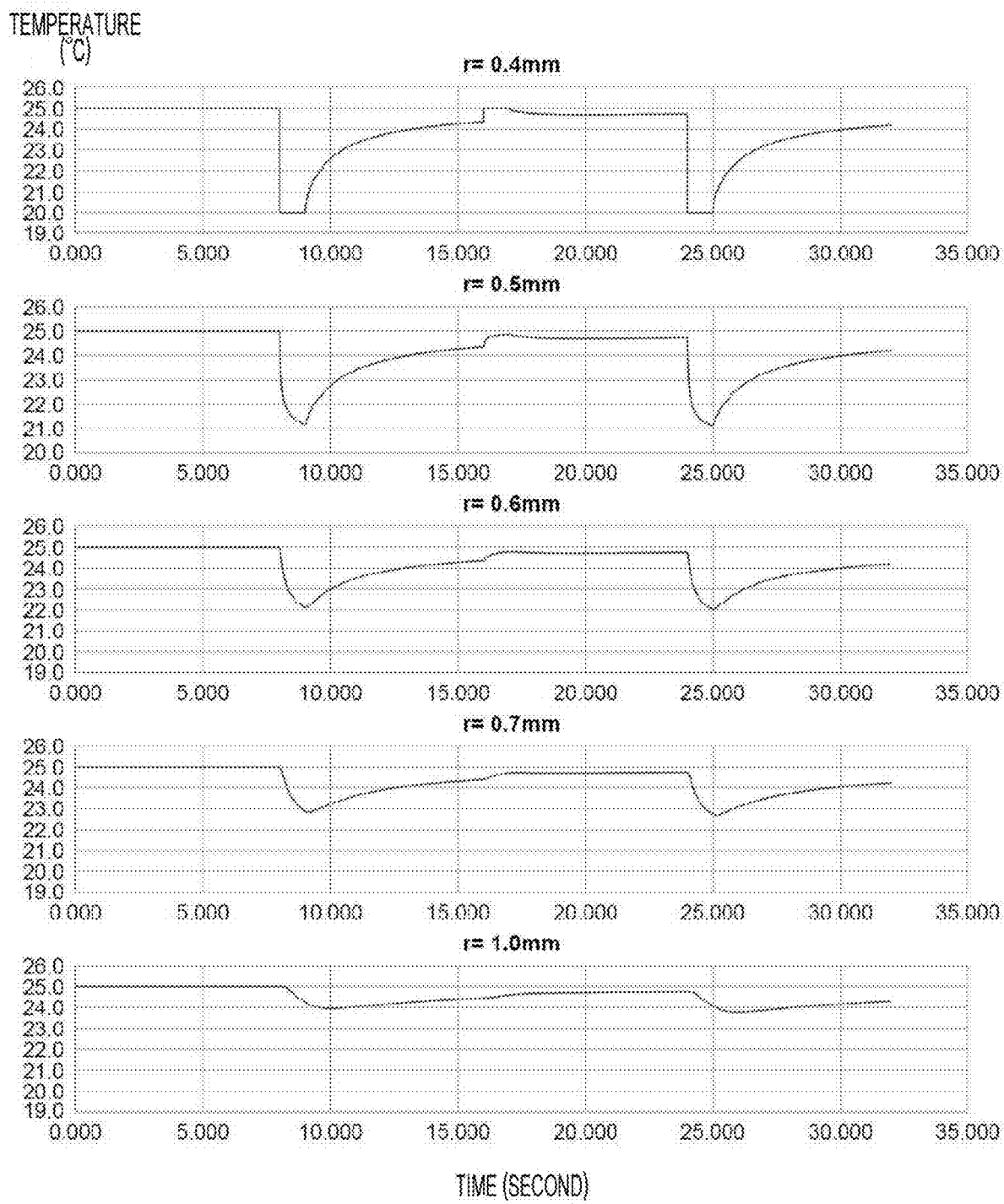
FIG. 10 illustrates a result of calculating a temporal temperature change of each coordinate on a dotted line r in FIG. 9 at the time of measurement in FIG. 4 using an equation of a one-dimensional nonstationary conductive heat transfer model in cylindrical coordinates.

FIG. 10 shows a result of calculating a temporal temperature change of each coordinate on the dotted line r in FIG. 9 at the time of measurement in FIG. 4 using an equation of a one-dimensional nonstationary conductive heat transfer model in cylindrical coordinates below, $$\frac{\partial T}{\partial t} = \alpha \left( \frac{\partial^2 T}{\partial r^2} + \frac{1}{r} \frac{\partial T}{\partial r} \right)$$

where T: temperature, t: time, r: r-coordinate in FIG. 9, and a: thermal diffusivity. In this calculation, simulation was performed on operation simulating the measurement in FIG. 4 in which an electrode and liquid in a flow path are initially constant at 25° C., liquid at 20° C. is fed to the flow path for one second, the liquid is stopped for seven seconds, the liquid at 25° C. is fed to the flow path for one second, the liquid is stopped for 7 seconds, and the liquid at 20° C. is fed again.

Since the flow path of the electrode has a radius of 0.5 mm, r=0.4 mm indicates temperature of liquid in the vicinity of a membrane in the flow path, r=0.5 mm indicates temperature of a sensitive membrane surface on the flow path side, r=0.6 mm indicates temperature of a portion 0.1 mm deeper than the membrane surface, r=0.7 mm indicates temperature of a portion 0.2 mm deeper than the membrane surface, and r=1.0 mm indicates temperature of a portion 0.5 mm deeper than the membrane surface. From the graph of r=0.4 mm, it can be seen that the liquid at 20° C. is warmed to 24° C. or more in seven seconds when liquid is stationary. Further, from the graph of r=0.5 mm corresponding to the membrane surface, it can be seen that temperature of the membrane surface decreases to around 21° C. when the liquid at 20° C. is fed. From the graphs of r=0.6, 0.7, and 1.0 mm, it can be seen that an inner portion of the membrane is less likely to be affected by a temperature fluctuation in the flow path.

Figure 11:
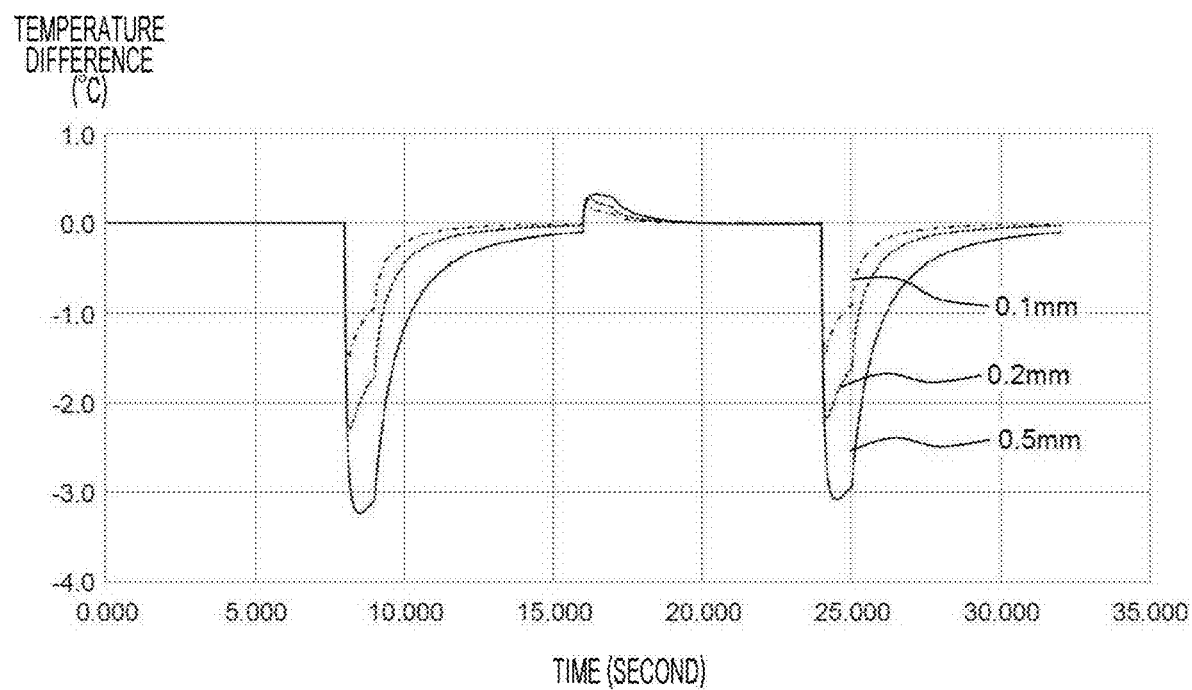
FIG. 11 shows a result of calculating a temperature difference between the front and back of a membrane for each of membrane thicknesses of 0.1 mm, 0.2 mm, and 0.5 mm.

FIG. 11 shows a result of calculating a temperature difference between the front and back of a membrane for each of cases of membrane thicknesses of 0.1 mm, 0.2 mm, and 0.5 mm. For example, a temperature difference between the front and back of a membrane having the membrane thickness of 0.1 mm can be calculated from a temperature difference between r=0.5 mm and r=0.6 mm. From this graph, it can be seen that when cold liquid is introduced into a flow path, in a case where a sensitive membrane is thick, an initial temperature difference between the front and back is large, and the temperature difference is eliminated relatively slowly. On the other hand, in a case where the sensitive membrane is thin, an initial temperature difference is small, and the temperature difference is eliminated quickly. Note that thermal diffusivity of the present conduction heat transfer model can be expressed by $\alpha = \lambda/\rho c$, where $\lambda$: thermal conductivity, $\rho$: density, and c: heat capacity. In the above calculation, calculation is performed assuming that a material of the sensitive membrane is a soft polyvinyl chloride membrane. However, in a case where the thermal diffusivity of the sensitive membrane is greatly different for each electrode, the calculation needs to be performed in consideration of not only the membrane thickness but also a difference in thermal diffusivity.

As described above, potential generated at an interface between a sensitive membrane and liquid in a flow path can be expressed by the Nernst equation, and has temperature dependency. Further, potential generated at an interface between a sensitive membrane and internal liquid can also be expressed by a similar equation, and since a direction of the potential with respect to a reference electrode is opposite to that on the flow path side on the circuit, the sign of the generated potential is opposite. Therefore, when temperature changes on the front and back of the sensitive membrane in the same manner, a potential change occurs so as to cancel each other out. Therefore, as the membrane thickness is thinner, a temperature difference between the front and back is less likely to occur, and thus a potential fluctuation when liquid having a temperature different from temperature of the sensitive membrane flows is small.

As described above, the case where liquid having extremely different temperatures are measured for easy recognizing of a potential fluctuation is described. However, even in a case where the temperature difference was small, a potential fluctuation according to the temperature difference was confirmed. Further, since heat conductivity is hardly related to ion concentration in liquid, a potential fluctuation according to a temperature change occurs similarly even in a specimen having different concentration.

A shape such as a diameter of a flow path also affects a temperature change of liquid in the flow path. Since heat capacity of liquid decreases as a flow path becomes narrower, a temperature change of the liquid in the flow path becomes faster. Conversely, a temperature change becomes slower as the flow path becomes thicker. In the present embodiment, a flow path diameter of an electrode is 1 mm, and it is considered to be easy to confirm a temperature change of liquid in a flow path on the order of several seconds.

Features of a potential fluctuation when a temperature difference between a sensitive membrane and liquid occurs are summarized as described below.

(Feature 1) Potential of a cation selective electrode is higher in a case where liquid temperature is lower than that of a sensitive membrane, and is lower in a case where the liquid temperature is higher than that of the sensitive membrane.

(Feature 2) Potential of an anion selective electrode is lower in a case where liquid temperature is lower than that of a sensitive membrane, and is higher in a case where the liquid temperature is higher than that of the sensitive membrane.

(Feature 3) The larger a temperature difference between a sensitive membrane and liquid temperature is, the larger potential fluctuates.

(Feature 4) When membrane thickness is large, a temperature difference between the front and back is likely to occur, and a potential fluctuation due to a change in liquid temperature is likely to occur.

(Feature 5) When liquid is stationary in a flow path, an electrode and the liquid exchange heat with each other, and a temperature difference between the electrode and the liquid is gradually reduced. The temperature difference calculator 181 calculates a temperature difference using a potential measurement result when liquid is stationary. However, even during liquid feeding, although different from that when liquid is stationary, heat exchange between an electrode and liquid is performed. Therefore, it is also possible to calculate a temperature difference using a potential measurement result at that time.

(Feature 6) The thinner a flow path, the faster liquid temperature approaches electrode temperature.

However, there is a case where a direction of a potential change in Feature 1 and Feature 2 is inverted as a circuit of the potential measurement unit 171 is changed.

Using these features, the temperature difference calculator 181 can calculate a temperature difference between a sensitive membrane and liquid according to a change in potential. That is, since an ion species to be measured of an electrode, membrane thickness of a sensitive membrane, and a diameter of a flow path are known, these parameters are substituted into a conduction heat transfer model for calculating a temperature difference between the front and back of the sensitive membrane described above, and an obtained curve is fitted to an actually measured potential curve in each electrode, so that a temperature difference can be calculated. At this time, temperature of liquid introduced into a flow path is assumed to be the same in all the electrodes.

Since there is a possibility that a change takes place due to a factor other than temperature if only potential information of one type of an electrode is used, it is desirable to perform analysis based on potential data of two or more types of electrodes. By analyzing potential of each electrode using known information in advance as described above, it is possible to easily determine whether a potential fluctuation is caused by a temperature difference.

The model used for the calculation may not be the above-described conduction heat transfer model. The configuration may be such that information on a potential fluctuation with respect to a change in liquid temperature is obtained in advance and stored in the temperature difference calculator 181, and the information on a curve and a slope of the potential fluctuation information is used so as to calculate a temperature difference from a potential change at the time of actual measurement, without using a theoretical model or the like.

First Embodiment: Example of Obtaining Temperature Difference from Conduction Heat Transfer Model The larger a temperature difference between liquid and an ion selective electrode (sensitive membrane) is, the larger electrode potential fluctuates during liquid introduction (Feature 3). The larger this potential fluctuation is, the larger a temporal change rate of the electrode potential is. In view of the above, as a conduction heat transfer model, a relationship between a temporal change rate of potential of an ion selective electrode and a temperature difference is defined in advance. The potential measurement unit 171 measures a temporal change rate of electrode potential. The temperature difference calculator 181 can acquire a temperature difference corresponding to an actual measurement result from a conduction heat transfer model by fitting the actual measurement result to the conduction heat transfer model.

Temporal change rates of a plurality of electrode potentials can be used as described below. First, for each electrode, a relationship between a temporal change rate of potential of an ion selective electrode and a temperature difference is defined in advance as a conduction heat transfer model. The potential measurement unit 171 measures a temporal change rate of each electrode potential. The temperature difference calculator 181 fits each actual measurement result to the conduction heat transfer model of each electrode. Based on a best fitting result (e.g., the least square sum of a difference between the model and the actual measurement result is the smallest), a temperature difference corresponding to an actual measurement result can be acquired from the conduction heat transfer model. In a case where the temperature differences obtained from each of the conduction heat transfer models are different from each other, an average or a weighted average of the temperature differences may be used. Alternatively, a single model encompassing the conduction heat transfer models of each electrode may be defined, and optimum fitting of a measurement result of each electrode may be obtained. The same applies to an example below.

Depending on whether an ion selective electrode reacts with a cation or an anion, electrode potential fluctuates upward or downward during liquid introduction (Features 1 and 2). In view of the above, as a conduction heat transfer model, a relationship between a type of an ion selective electrode and potential increase/decrease at the time of liquid introduction is defined in advance. The potential measurement unit 171 measures increase or decrease of each electrode potential at the time of liquid introduction. The temperature difference calculator 181 can acquire a temperature difference corresponding to an actual measurement result from a conduction heat transfer model by fitting the actual measurement result to the conduction heat transfer model. Specifically, as a conduction heat transfer model, a relationship between an increment (the increment here includes a negative increment) of each electrode potential at the time of liquid introduction and a temperature difference is defined in advance. The temperature difference calculator 181 can acquire a corresponding temperature difference from the conduction heat transfer model by fitting an actual measurement result of the increment to the conduction heat transfer model.

The thicker the ion sensitive membrane, the larger the fluctuation of electrode potential due to a temperature difference at the time of liquid introduction (Feature 4). In view of the above, as a conductive heat transfer model, a relationship between membrane thickness of a sensitive membrane/potential fluctuation corresponding to membrane thickness/temperature difference/is defined in advance. The temperature difference calculator 181 can fit a potential fluctuation at the time of liquid introduction and known membrane thickness to the conduction heat transfer model so as to acquire a temperature difference corresponding to these from the conduction heat transfer model.

There is a case where thickness of a sensitive membrane is different for each ion selective electrode. In this case, as a conduction heat transfer model, a relationship between membrane thickness of a sensitive membrane/potential fluctuation corresponding to membrane thickness/temperature difference is defined in advance for each electrode. The temperature difference calculator 181 can obtain a temperature difference by fitting each actual measurement result and membrane thickness of each electrode to the conduction heat transfer model of each electrode.

As thickness of a sensitive membrane is thicker, a temperature difference between the front and back of the sensitive membrane is more slowly eliminated (Feature 4). That is, a temporal change of a temperature difference and membrane thickness have a correspondence relationship. In view of the above, as a conduction heat transfer model, a relationship between: a temporal change of a temperature difference between the front and back of a sensitive membrane; and membrane thickness; is defined in advance. The temperature difference calculator 181 can fit elapsed time from introduction of liquid into a flow path and known membrane thickness to the conduction heat transfer model so as to acquire a temperature difference corresponding to these from the conduction heat transfer model. In a case where membrane thickness is different for each electrode, the conduction heat transfer model only needs to be similarly defined for each electrode.

The thinner a sensitive membrane, the smaller a fluctuation in electrode potential at the time of liquid introduction (Feature 4). In view of the above, as a conduction heat transfer model, a relationship between a fluctuation of electrode potential at the time of liquid introduction and membrane thickness is defined in advance. The temperature difference calculator 181 can fit an increment of electrode potential when liquid is introduced into a flow path and known membrane thickness to the conduction heat transfer model so as to acquire a temperature difference corresponding to these from the conduction heat transfer model.

The thinner a flow path, the more quickly a temperature difference decreases between liquid and an electrode when the liquid is stationary (Feature 6). In view of the above, as a conduction heat transfer model, a relationship between: a temporal change of a temperature difference between liquid and an electrode; and a flow path diameter; is defined in advance. The temperature difference calculator 181 can fit elapsed time from introduction of liquid into a flow path and a known flow path diameter to the conduction heat transfer model so as to acquire a temperature difference corresponding to these from the conduction heat transfer model.

It is also possible to use only a part of the conduction heat transfer models described above, or a conduction heat transfer model including two or more of the models described above may be constructed. For example, a conduction heat transfer model defining a relationship between a temporal change rate of electrode potential/membrane thickness/a temperature difference can be constructed, and an actual measurement result of a temporal change rate of electrode potential and known membrane thickness can be fitted to the model.

Second Embodiment

The temperature difference calculator 181 may correct a potential measurement value measured by the potential measurement unit 171 according to a calculated temperature difference. Specifically, by predicting a temporal change of potential measured by the potential measurement unit 171 according to a temporal change rate of electrode potential in a conduction heat transfer model, electrode potential at any time after liquid introduction can be estimated. A result of the estimation may be used as a corrected value of electrode potential. Alternatively, accuracy of correction is improved by using temperature simulation of each of the front and back of a sensitive membrane.

As to correction of a potential measurement value in a case where the entire system changes in temperature instead of a temperature difference between a sensitive membrane and liquid, correction can be made based on the Nernst equation or the tendency of a potential fluctuation specific to an electrode or a device acquired in advance using information from a temperature sensor attached to the electrode temperature control mechanism 184.

Third Embodiment

In a third embodiment of the present invention, a timing at which the temperature difference calculator 181 calculates a temperature difference and a method of feeding back the calculated temperature difference will be described. A configuration of the device 100 for measuring electrolyte concentration is similar to that of the first to second embodiments.

At the time of start-up of a device, internal standard solution is measured at regular time intervals in order to confirm whether temperature is stabilized. The temperature difference calculator 181 calculates a temperature difference, performs calibration after confirming that the temperature difference is within a specified value, and analyzes a specimen. In the prior art, analysis is started after a sufficiently long time elapses from starting up the device. However, depending on an installation environment of the device such as room temperature or water temperature, the time may be longer than necessary. For this reason, by measuring a temperature difference at the time of start-up as described above, it is possible to start analysis in a necessary and sufficient time, leading to reduction in start-up time. Further, even in a case where temperature is not sufficiently stable, the potential correction described in the second embodiment enables measurement from immediately after start-up, which is a great advantage for the user.

A temperature difference may also be calculated at the time of calibration or specimen analysis. A temperature difference can be calculated from a potential change of internal standard solution measured before and after specimen measurement. Further, in a specimen in which concentration varies every time, an absolute value of potential varies depending on ion concentration in the specimen. However, a temperature difference can be calculated from a change in potential when liquid is stationary.

As described above, a temperature difference can be monitored not only at the time of measurement of internal standard solution but also at the time of measurement of standard solution or a specimen. For this reason, in a case where a tendency that liquid temperature gradually deviates although it is within a specified value is detected, output of a temperature control mechanism of liquid or a temperature control mechanism of an electrode is adjusted, and the temperature deviation can be reduced even during continuous measurement. Note that, since potential used for concentration calculation is acquired when several seconds elapse after liquid becomes stationary, a temperature difference between liquid and a sensitive membrane is alleviated to some extent, and there is comparatively less influence of a temperature change of liquid. For this reason, it is possible to perform temperature adjustment during continuous measurement as described above.

When analysis is resumed after measurement is stopped for a while, liquid is usually discarded or the like until temperature is in a steady state, and thus, it takes time for that. Also in this case, it is possible to improve the analysis accuracy and shorten return time by confirming that temperature is adjusted, by performing output control of a temperature control mechanism, by performing potential correction, and the like. Further, when a large temperature difference is detected suddenly, the temperature difference is output as an error, and reanalysis can be performed without employing an analysis result at that time.

By measuring a change in a temperature difference when output of a temperature control mechanism is changed in advance and storing data of responsiveness of an output control mechanism in the temperature difference calculator 181, it is easy to accurately perform feedback to output control when a temperature difference occurs during analysis.

In the above description, concentration measurement and temperature difference calculation are performed using potential acquired when liquid is stationary, but these may be performed using potential during liquid feeding. In that case, since liquid temperature in a flow path and a manner of temperature change of a sensitive membrane change, it is necessary to perform temperature difference calculation and correction corresponding to the change.

Variation of Present Invention

The present invention is not limited to the above embodiments and includes a variety of variations. For example, the above embodiments are described in detail for easy understanding of the present invention, and the present invention is not necessarily limited to embodiments that include all the described configurations. Part of a configuration of a certain embodiment can be replaced with a configuration of another embodiment, and a configuration of a certain embodiment can be added to a configuration of another embodiment. Further, for part of a configuration of each embodiment, other configurations may be added, removed, or replaced with.

In the above embodiment, the temperature control mechanism is not necessarily required as long as a temperature difference between liquid and a sensitive membrane is calculated from a potential change or potential is only corrected using the temperature difference. Further, configurations of the comparative electrode and the liquid junction portion are not limited to those described above. The ion selective electrode is not limited to an internal liquid type, and may have another configuration such as a solid electrode.

In the above embodiment, a conduction heat transfer model can be configured by storing data such as a mathematical expression and a numerical value describing the model in a storage device. The storage device can be configured as, for example, a storage device such as a memory internally provided in the device controller 175, but is not limited to this, and another appropriate storage device may be used. Another functional unit may store the model data.

In the above embodiment, the device controller 175, the concentration calculator 172, and the temperature difference calculator 181 can be configured by hardware such as a circuit device in which functions of the units are mounted, or can be configured by an arithmetic device such as a central processing unit (CPU) executing software on which these functions are mounted.

REFERENCE SIGNS LIST 4 electrode housing
11 electrode housing
12 flow path
13 internal electrode
15 packing
16 internal liquid
17 ion sensitive membrane
18 lid
101 chlorine ion electrode
102 potassium ion electrode
103 sodium ion electrode
104 comparative electrode
105 pinch valve
106 vacuum suction nozzle
107 sipper nozzle
108 diluent supply nozzle
109 internal standard solution supply nozzle
110 dilution tank
111 waste liquid tank
121, 122, 125 electromagnetic valve
131 internal standard solution syringe pump
132 diluent syringe pump
133 sipper syringe pump
141 internal standard solution bottle
151 diluent bottle
161 comparative electrode liquid bottle
171 potential measurement unit
172 concentration calculator
174 output unit
175 device controller
176 input unit
181 temperature difference calculator
182 temperature controller

The invention claimed is:

1. A device for measuring electrolyte concentration that measures concentration of an ion in liquid using an ion selective electrode, the device comprising:
    a potential measurement unit that measures potential of the ion selective electrode at least two or more different times while the liquid is present in a flow path for introducing the liquid into the ion selective electrode;
    a central processing unit (CPU) configured to:
        calculate the concentration by using potential of the ion selective electrode; and
        calculate a temperature difference between the liquid and the ion selective electrode using potential of the ion selective electrode at two or more different times measured by the potential measurement unit; and
    a temperature controller configured to control at least one of temperature of the liquid or temperature of the ion selective electrode based on the calculated temperature difference to improve measurement accuracy.

2. The device for measuring electrolyte concentration according to claim 1, wherein
    the ion selective electrode has a potential change characteristic in which potential of the ion selective electrode changes with respect to time at a temporal change rate corresponding to a temperature difference between the liquid and the ion selective electrode,
    the potential measurement unit measures a temporal change rate of potential of the ion selective electrode, and
    the CPU calculates a temperature difference between the liquid and the ion selective electrode by comparing a temporal change rate of potential of the ion selective electrode measured by the potential measurement unit with the potential change characteristic.

3. The device for measuring electrolyte concentration according to claim 1, wherein
    the ion selective electrode includes a first electrode that reacts with a first ion and a second electrode that reacts with a second ion,
    the first electrode has a characteristic in which potential of the first electrode changes at a first change rate with respect to time when a temperature difference between the liquid and the first electrode is a first temperature,
    the second electrode has a characteristic in which potential of the second electrode changes at a second change rate with respect to time when a temperature difference between the liquid and the second electrode is the first temperature, the potential measurement unit measures a temporal change rate of potential of the first electrode and a temporal change rate of potential of the second electrode, and the CPU compares a temporal change rate of potential of the first electrode measured by the potential measurement unit with the first change rate, and compares a temporal change rate of potential of the second electrode measured by the potential measurement unit with the second change rate, thereby calculating a temperature difference between the liquid and the ion selective electrode.

4. The device for measuring electrolyte concentration according to claim 1, wherein the ion selective electrode includes a first electrode that reacts with a first ion and a second electrode that reacts with a second ion, the first electrode is configured such that in a case where temperature of the liquid is lower than temperature of a first sensitive membrane of the first electrode, potential of the first electrode increases when the liquid is introduced into the first electrode, and in a case where temperature of the liquid is higher than temperature of the first sensitive membrane, potential of the first electrode decreases when the liquid is introduced into the first electrode, the second electrode is configured such that in a case where temperature of the liquid is lower than temperature of a second sensitive membrane of the second electrode, potential of the second electrode decreases when the liquid is introduced into the second electrode, and in a case where temperature of the liquid is higher than temperature of the second sensitive membrane, potential of the second electrode increases when the liquid is introduced into the second electrode, the potential measurement unit measures potential of the first electrode when the liquid is introduced and potential of the second electrode when the liquid is introduced, and the CPU calculates a temperature difference between the liquid and the ion selective electrode according to increase or decrease in potential of the first electrode when the liquid is introduced and increase or decrease in potential of the second electrode when the liquid is introduced.

5. The device for measuring electrolyte concentration according to claim 4, wherein the first electrode is configured such that in a case where temperature of the liquid is lower than temperature of the first sensitive membrane, potential of the first electrode increases by a first potential value when the liquid is introduced into the first electrode, and in a case where temperature of the liquid is higher than temperature of the first sensitive membrane, potential of the first electrode decreases by a second potential value when the liquid is introduced into the first electrode, the second electrode is configured such that in a case where temperature of the liquid is lower than temperature of the second sensitive membrane, potential of the second electrode decreases by a third potential value when the liquid is introduced into the second electrode, and in a case where temperature of the liquid is higher than temperature of the second sensitive membrane, potential of the second electrode increases by a fourth potential value when the liquid is introduced into the second electrode, and the CPU calculates a temperature difference between the liquid and the ion selective electrode by using an increment of potential of the first electrode when the liquid is introduced and an increment of potential of the second electrode when the liquid is introduced.

6. The device for measuring electrolyte concentration according to claim 1, wherein the ion selective electrode includes a sensitive membrane that reacts with the ion, the ion selective electrode is configured such that when the liquid is introduced into the ion selective electrode, potential of the ion selective electrode fluctuates by a potential value corresponding to thickness of the sensitive membrane and to a temperature difference between the ion selective electrode and the liquid, and the CPU calculates a temperature difference between the liquid and the ion selective electrode by using an increment of potential of the ion selective electrode when the liquid is introduced.

7. The device for measuring electrolyte concentration according to claim 6, wherein the ion selective electrode includes a first electrode having a first sensitive membrane having a first thickness and a second electrode having a second sensitive membrane having a second thickness, the first electrode is configured such that potential of the first electrode fluctuates by a first potential value when the liquid is introduced into the first electrode, the second electrode is configured such that potential of the second electrode fluctuates by a second potential value when the liquid is introduced into the second electrode, and the CPU calculates a temperature difference between the liquid and the ion selective electrode according to an increment of potential of the first electrode when the liquid is introduced and an increment of potential of the second electrode when the liquid is introduced.

8. The device for measuring electrolyte concentration according to claim 1, wherein the CPU calculates a temperature difference between the liquid and the ion selective electrode using potential of the ion selective electrode measured by the potential measurement unit when the liquid is stationary in the flow path.

9. The device for measuring electrolyte concentration according to claim 1, wherein the ion selective electrode includes a sensitive membrane that reacts with the ion, the ion selective electrode has a temperature characteristic in which, when the liquid is introduced into the flow path, a temperature difference corresponding to thickness of the sensitive membrane is generated between opposing surfaces of the sensitive membrane, and the temperature difference decreases with time at a temporal change rate corresponding to thickness of the sensitive membrane, and the CPU calculates a temperature difference between the liquid and the ion selective electrode according to elapsed time from introduction of the liquid into the flow path and thickness of the sensitive membrane.

10. The device for measuring electrolyte concentration according to claim 1, wherein the ion selective electrode includes a sensitive membrane that reacts with the ion, the ion selective electrode has a potential fluctuation characteristic in which potential of the ion selective electrode fluctuates according to thickness of the sensitive membrane when the liquid is introduced into the flow path, and the CPU calculates a temperature difference between the liquid and the ion selective electrode according to an increment of potential of the ion selective electrode when the liquid is introduced and thickness of the sensitive membrane.

11. The device for measuring electrolyte concentration according to claim 1, wherein the ion selective electrode has a temperature change characteristic in which a temperature difference between the liquid and the ion selective electrode decreases with time at a temporal change rate corresponding to thickness of the flow path, and the CPU calculates a temperature difference between the liquid and the ion selective electrode according to elapsed time from when introducing the liquid into the flow path to when measuring potential of the ion selective electrode by the potential measurement unit.

12. The device for measuring electrolyte concentration according to claim 1, wherein the CPU corrects potential of the ion selective electrode measured by the potential measurement unit according to a correspondence relationship between the calculated temperature difference and potential measured by the potential measurement unit, and the CPU calculates the concentration using potential of the ion selective electrode corrected by the temperature difference calculator the CPU.

13. The device for measuring electrolyte concentration according to claim 2, wherein the CPU interpolates a temporal change rate of potential of the ion selective electrode according to the potential change characteristic, thereby correcting potential of the ion selective electrode measured by the potential measurement unit.

14. The device for measuring electrolyte concentration according to claim 1, wherein the temperature controller controls the at least one of temperature of the liquid or temperature of the ion selective electrode so as to reduce a temperature difference between the liquid and the ion selective electrode calculated by the CPU.

15. The device for measuring electrolyte concentration according to claim 1, wherein the CPU calculates a temperature difference between the liquid and the ion selective electrode in at least one of cases where the device for measuring electrolyte concentration is started, where calibration with respect to a calibration curve used by the CPU is performed, or where the concentration is measured.

16. The device for measuring electrolyte concentration according to claim 1, wherein the CPU is configured to correct subsequent concentration measurements using the calculated temperature difference.

17. A device for measuring electrolyte concentration that measures concentration of an ion in liquid using an ion selective electrode, the device comprising:

a potential measurement unit that measures potential of the ion selective electrode at least two or more different times while the liquid is present in a flow path for introducing the liquid into the ion selective electrode;

a central processing unit (CPU) configured to:

calculate the concentration by using potential of the ion selective electrode;

calculate a temperature difference between the liquid and the ion selective electrode using potential of the ion selective electrode at two or more different times measured by the potential measurement unit, and correct subsequent concentration measurements using the calculated temperature difference.

* * * * *